United States Patent [19]

Alchermes et al.

[11] Patent Number: 5,112,334
[45] Date of Patent: May 12, 1992

[54] SURGICAL INSTRUMENT FOR FACILITATING ACCURATE OSTEOTOMY CUTS IN BONE AND METHOD FOR UTILIZING SAME

[76] Inventors: Stephen L. Alchermes, 43 Duck Pond Rd.; Mark A. Lombardo, 7 Landing Rd., both of Glen Cove, N.Y. 11542

[21] Appl. No.: 604,077

[22] Filed: Oct. 25, 1990

[51] Int. Cl.$^5$ .............................................. A61B 17/00
[52] U.S. Cl. ..................................... 606/87; 606/102; 606/103; 606/79
[58] Field of Search ...................... 606/86, 87, 88, 89, 606/102, 167, 170, 174, 103, 79, 83; 30/257

[56] References Cited

U.S. PATENT DOCUMENTS

| | | | |
|---|---|---|---|
| 2,136,414 | 11/1938 | Clements | 606/174 |
| 2,250,638 | 2/1940 | Kubinec | 30/257 |
| 3,740,779 | 6/1973 | Rubricuis | 606/167 |
| 4,349,058 | 9/1982 | Comparetto | 606/87 |

FOREIGN PATENT DOCUMENTS

| | | | |
|---|---|---|---|
| 925334 | 5/1982 | U.S.S.R. | 606/122 |

*Primary Examiner*—Robert A. Hafer
*Assistant Examiner*—David Kenealy
*Attorney, Agent, or Firm*—Allen R. Morganstern

[57] ABSTRACT

The present invention is directed to a new and improved surgical instrument capable of facilitating as well as accurately assisting in the achieving of acute angle osteotomy cuts in bone. The benefits are achieved as a result of the instrument's structural elements comprising a calibration arm elevated above a pedestal member by way of an elevational member, there being structurally affixed to said pedestal member an aligning member. By having structurally affixed to the pedestal member by way of pin fastening means a second pedestal member capable of pivotal movement about the pin fastening means and which is capable of interaction with the calibration arm of the surgical instrument as well as defining an additional aligning member adjacent to the pin fastening means, there is achieved the ability to selectively define between the respective aligning members of the surgical instrument an acute angle that is selectively and accurately determined for purposes of acting as a guide for making acute angle osteotomy cuts in bone.

7 Claims, 2 Drawing Sheets

ID FOR TOTAL KNEE REPLACEMENT"; U.S.

SURGICAL INSTRUMENT FOR FACILITATING ACCURATE OSTEOTOMY CUTS IN BONE AND METHOD FOR UTILIZING SAME

SUMMARY OF THE INVENTION

The present invention is directed to a new and improved surgical instrument capable of facilitating as well as accurately assisting in the achieving of acute angle osteotomy cuts in bone. The benefits are achieved as a result of the instrument's structural elements comprising a calibration arm elevated above a pedestal member by way of an elevational member, there being structurally affixed to said pedestal member an aligning member. By having structurally affixed to the pedestal member by way of pin fastening means a second pedestal member capable of pivotal movement about the pin fastening means and which is capable of interaction with the calibration arm of the surgical instrument as well as defining an additional aligning member adjacent to the pin fastening means, there is achieved the ability to selectively define between the respective aligning members of the surgical instrument an acute angle that is selectively and accurately determined for purposes of acting as a guide for making acute angle osteotomy cuts in bone.

BACKGROUND AND OBJECTS OF THE INVENTION

The present invention relates generally to a new and improved surgical instrument capable of facilitating as well as accurately assisting in the achieving of acute angle osteotomy cuts in bone.

Although prior art devices existed prior to the present invention that addressed themselves to appliances and/or devices that assisted in medical procedures whereby a physician made an acute angle osteotomy cut in a bone, none of the prior art devices achieve the advantages of the present invention nor are such prior art devices capable of providing the overall achievements consistent with the present design.

In conjunction with the above, it should be noted that the prior art considered relevant to date by applicants, but which does not anticipate nor teach the present invention is as follows. More particularly, reference is made to U.S. Pat. No. 4,768,504 to Hans G. Ender, entitled "DEVICE FOR OSTEOTOMY"; U.S. Pat. No. 4,750,481, to H. William Reese, entitled, "OSTEOTOMY APPLIANCES AND METHOD"; U.S. Pat. No. 4,565,191, to D. Barclay Slocum, entitled, "APPARATUS AND METHOD FOR PERFORMING CUNEIFORM OSTEOTOMY"; U.S. Pat. No. 4,501,268, to John E. Comparetto, entitled, "BONE WEDGE GUIDANCE SYSTEM"; U.S. Pat. No. 4,457,307, to William T. Stillwell, entitled, "BONE CUTTING DEVICE FOR TOTAL KNEE REPLACEMENT"; U.S. Pat. No. 4,349,018, to Gary R. Chambers, entitled, "OSTEOTOMY APPARATUS"; and U.S. Pat. No. 4,335,715, to William H. Kirkley, entitled, "OSTEOTOMY GUIDE".

In keeping with the invention, it is therefore an object of this invention to create a new and improved surgical instrument and method of utilizing same that is capable of facilitating as well as accurately assisting a physician in the achieving of acute angle osteotomy cuts in bone.

It is another object of the invention to create a new and improved surfical instrument and method of utilizing same that is capable of facilitating as well as accurately assisting a physician in the achieving of acute angle osteotomy cuts in bone wherein there is further achieved the ability to accurately provide a means to achieve a pre-determined angle associated with said cut in a bone without the necessity of guessing and/or approximating same.

It is another object of the invention to create a new and improved surgical instrument and method of utilizing same that is capable of facilitating as well as accurately assisting a physician in the achieving of acute angle osteotomy cuts in bone wherein upon the utilization of said surgical instrument, there is avoided, as said cut is made in the bone, deviation from the desired angle as related thereto.

It is another object of the invention to create a new and improved surgical instrument and method of utilizing same that is capable of facilitating as well as accurately assisting a physician in the achieving of acute angle osteotomy cuts in bone wherein there is provided outside of the surgical area for ready visualization the shaped osteotomy before cutting of the bone occurs.

It is another object of the invention to create a new and improved surgical instrument and method of utilizing same that is capable of facilitating as well as accurately assisting a physician in the achieving of acute angle osteotomy cuts in bone wherein there is achieved the ability to minimize the size of the wound exposure associated with an osteotomy cut in a bone, since inherent in said design is the positioning of the calibration arm of the device outside of and otherwise above the operative area.

It is another object of the invention to create a new and improved surgical instrument and method of utilizing same that is capable of facilitating as well as accurately assisting a physician in the achieving of acute angle osteotomy cuts in bone wherein said instrument provides for a double fixation of the device against the bone involved in the surgical procedure so as to prevent movement of the instrument in relationship to the bone undergoing an osteotomy cut thereby avoiding a cut in said bone that deviates from the desired angle.

It is another object of the invention to create a new and improved surgical instrument and method of utilizing same that is capable of facilitating as well as accurately assisting a physician in the achieving of acute angle osteotomy cuts in bone wherein upon utilization of the surgical instrument at the operative site, the placement thereof adjacent to the bone that is to undergo an osteotomy cut is achieved through utilizing portions of the instrument that extends above said operative site.

The objects and advantages of the invention are set forth in part herein and in part will be obvious herefrom, or may be learned by practice of the invention, the same being realized and attained by means of the instrumentalities and combinations pointed out in the appended claims.

The invention consists in the novel parts, constructions, arrangements, combinations and improvements hereto shown and described.

SUMMARY OF THE INVENTION

Figure 1:
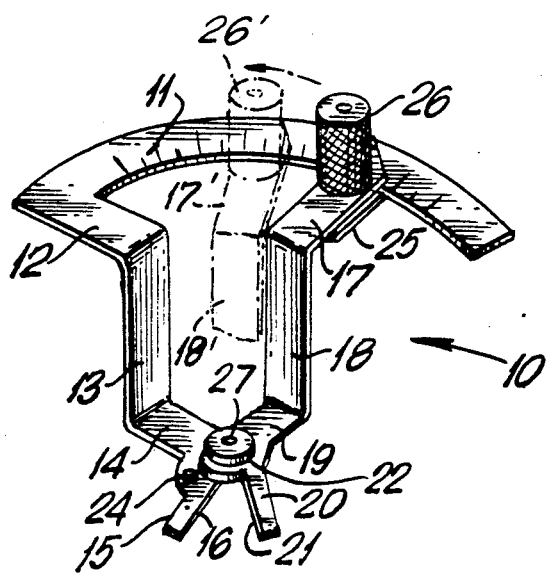
FIG. 1 is a three dimensional perspective view of the surgical instrument constructed in accordance with the invention as seen from a vantage point positioned in front of as well as above the instrument.

Referring now more particularly to the embodiment of the above invention as illustrated in the accompanying drawings, reference is now made to FIG. 1 wherein a three dimensional perspective view of surgical instrument 10 constructed in accordance with the invention as seen from a vantage point positioned in front of as well as above surgical instrument 10.

As therein illustrated, surgical instrument 10 comprises a calibration arm 11 defining a portion of a circular arc having angle member 12 structurally affixed to said calibration arm 11, calibration arm 11 and angle member 12 appearing within the same plane, angle member 12 being aligned parallel to the radius that defines the arc of calibration arm 11. Structurally affixed to angle member 12 is elevation member 13, elevation member 13 being at right angles to the plane defined by calibration arm 11 and angle member 12. Additionally elevation member 13 is structurally affixed to pedestal member 14, elevation member 13 being at right angles to pedestal member 14. Additionally, calibration 11, angle member 12, elevation member 13 and pedestal member 14 all define a singular unitary structure. Furthermore, the plane defined by calibration arm 11 and angle member 12 is parallel to the plane defined by pedestal member 14, the vertical distance between said respective parallel planes being that equivalent to elevation member 13.

In further keeping with the invention, pedestal member 14 has structurally affixed to it aligning member 15, aligning member 15 being in the same plane as defined by pedestal member 14, aligning member 15 and pedestal member 14 defining a unitary structure.

In further keeping with the invention, aligning member 15 defines guiding edge 16 which, in accordance with the utilization of surgical instrument 10, provides one of the measuring and/or guiding edges in conjunction with the utilization of the invention.

As further depicted in FIG. 1, surgical instrument 10 further comprises indicator arm 17, elevation member 18, pedestal member 19, aligning member 20 and guiding edge 21.

As depicted in FIG. 1, there is structurally affixed to indicator arm 17 elevation member 18, elevation member 18 being at right angles to the plane that indicator arm 17 defines. Furthermore, the plane defined by indicator arm 17 is parallel to the plane defined by calibration arm 11 and angle member 12.

As further illustrated in FIG. 1, elevation member 18 is structurally affixed to indicator arm 17, elevation member 18 being at right angles to indicator arm 17. Additionally, elevation member 18 is structurally affixed to pedestal member 19, elevation member 18 being at right angles to pedestal member 19, it being consistent with the invention that indicator arm 17, elevation member 18 and pedestal member 19 all defining a singular unitary structure such that the plane defined by indicator arm 17 is parallel to the plane defined by pedestal member 19, the vertical distance between said respective planes being that equivalent to elevation member 18.

In further keeping with the invention, pedestal member 19 has structurally affixed to it aligning member 20, aligning member 20 being in the same plane as defined by pedestal member 19, aligning member 20 and pedestal member 19 defining a unitary structure.

In further keeping with the invention, aligning member 20 defines guiding edge 21 which, in accordance with the utilization of surgical instrument 10, provides one of the measuring and/or guiding edges in conjunction with the utilization of the invention.

As further illustrated in FIG. 1, pedestal member 19 and pedestal member 14, each have defined through their structure an opening capable of receiving fastening pin 22 with fastening member 23 as therein illustrated such that there is created a rotational interfit between pedestal member 14 and pedestal member 19 such that each is capable of rotational movement about the axis of fastening pin 22.

As further illustrated in FIG. 1, there is formed throughout the entire vertical length of fastening pin 22 a cylindrical opening 27, the axis of cylindrical opening 27 being coincident with the vertical axis of fastening pin 22.

More particularly, the structure defined by indicator arm 17, elevation member 18, pedestal member 19 and aligning member 20 is pivotally affixed to the structure defined by angle member 12, elevation member 13, pedestal member 14 and aligning member 15 by the placement of the respective defined structures one on top of each other as illustrated in FIG. 1 and centered about the hole formed through pedestal member 19 and pedestal member 14 respectively, which has fastening pin 22 passing there through so as to provide an axis of rotation thereabout as related to said respective structures.

It should be noted that with regard to fastening pin 22, that aside from providing the structural means for fastening pedestal member 19 to pedestal member 14 while allowing for the rotational movement about the axis of fastening pin 22 of said respective elements, fastening pin 22 further defines a cylindrical opening 27 throughout its entire length coincident with its axes, the utilization of cylindrical opening 27 to be more fully discussed hereinafter in conjunction with the implementation of various medical procedures which utilize said surgical instrument 10.

In further keeping with the invention and as illustrated in FIG. 1, there is further structurally affixed to aligning member 15, a spike member 24, spike member 24 providing means to anchor surgical instrument 10 to bone during utilization of surgical instrument 10 so as to avoid movement thereof from a desired position.

Additionally, indicator arm 17 has structurally affixed to its underneath side arm member 25 such that the end of arm member 25 adjacent to elevation member 18 is structural bonding affixed to indicator arm 17 while the other end of arm member 25 defines a spaced opening between itself and indicator arm 17 so as to allow for the position therebetween of calibration arm 11 as illustrated in FIG. 1. By having screw member 26 pass through an opening formed through indicator arm 17 and in threaded alignment with the opening formed in arm member 25 that is capable of receiving the threaded portion of said screw member 26, there is affixed a means, by which, upon rotation of screw member 26 about its axis, there is cause through the interaction of the threaded portion of screw member 26 with the compatible threaded opening formed in arm member 25 the frictional compression of arm member 25 against indicator arm 17 so as to pinch in tight alignment same and thus positioning indicator arm 17 in association with calibration arm 11 into a locked position. In so doing, there is achieved the selective positioning and locking into place of guiding edge 16 in relationship to guiding edge 21 in accordance with the invention.

Furthermore, and in keeping with the invention, calibration arm 11 has formed within its top surface calibration markings capable of defining the acute angle defined between guiding edge 16 and guiding edge 21 thereby enabling one to selectively set the desired angle between guiding edge 16 and guiding edge 21. As indicated in FIG. 1, there is attempted to be illustrated in physical movement of screw member 26, indicator arm 17 and a portion of elevational member 18 from the position illustrated therein to a position to the left thereof (as indicated by the dashed arrow adjacent to screw member 26) as would be the case should there be the desire to increase the angle defined between guiding edge 16 and guiding edge 21, same being illustrated by the dashed lines that depict 26', 17' and 18' which correspond to screw member 26, indicator arm 17 and elevational member 18 respectively.

Figure 2:
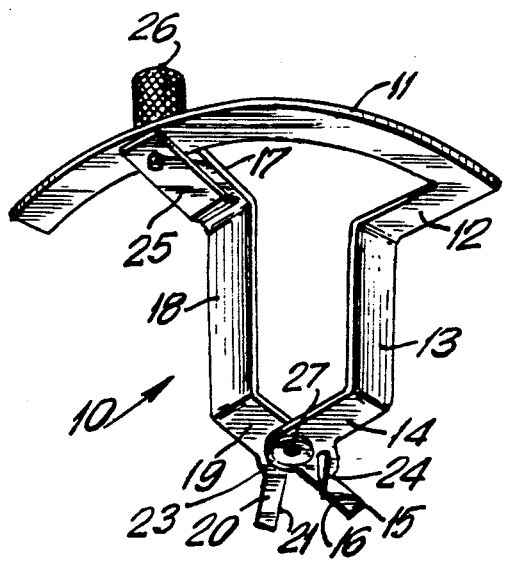
FIG. 2 is a three dimensional perspective view of the surgical instrument constructed in accordance with the invention as seen from a vantage point positioned behind as well as below the instrument.
Figure 3:
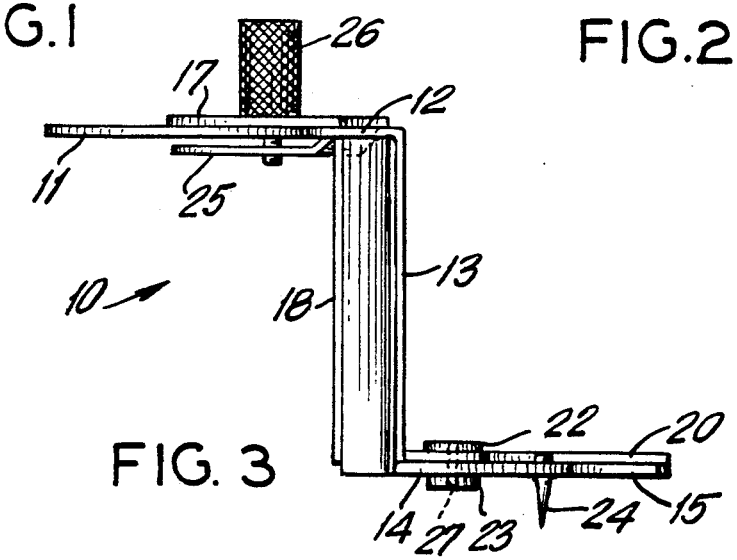
FIG. 3 is a left side elevational view of the surgical instrument as depicted in FIG. 1 of the drawings.
Figure 4:
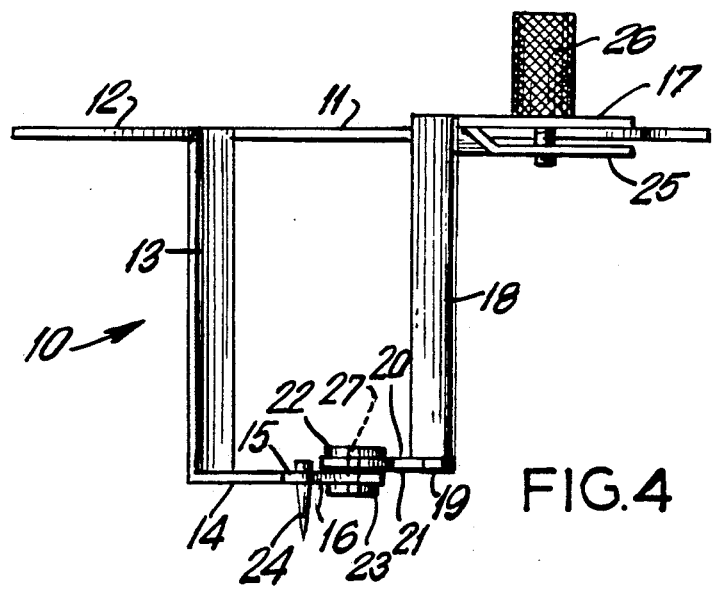
FIG. 4 is a front elevational view of the surgical instrument as depicted in FIG. 1.

In accordance with the invention and as previously indicated, FIG. 3 is a left side elevational view of surgical instrument 10 as depicted in FIG. 1 while FIG. 4 is a front elevational view of surgical instrument 10 as depicted in FIG. 1. Furthermore, FIG. 2 is a three dimensional perspective view of surgical instrument 10 as seen from a vantage point positioned behind as well as below said instrument.

In accordance with the invention, it should be noted that surgical instrument 10 in its preferred embodiment and use, is to be utilized in conjunction with certain surgical procedures which seek to achieve an acute angle osteotomy cut in a bone. In conjunction therewith, in achieving said cut, as would be the case in conjunction with a cut of bone at the medial surface of the first metatarsal head, there is first conducted an incision at the point of interest so as to draw back muscle and other soft tissue away from the bone in question.

Figure 5:
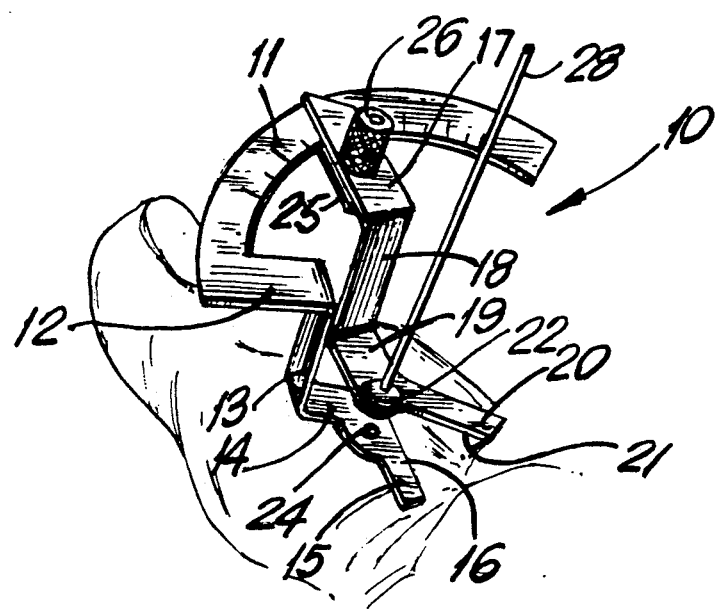
FIG. 5 is a three dimensional perspective view of the surgical instrument constructed in accordance with the invention as utilized in conjunction with an operative procedure associated with the medial surface of the first metatarsal head of an individual's foot.

Reference is now herein made to FIG. 5 wherein there is illustrated a three dimensional perspective view of the surgical instrument 10 constructed in accordance with the invention as utilized in conjunction with an operative procedure associated with the medial surface of the first metatarsal head of an individual's foot. In keeping with the invention, as depicted in FIG. 5, there is illustrated therein the insertion of surgical spike 28 into the bone in question as depicted in FIG. 5 at a point envisioned as related thereto to be the apex of the acute angular cut intended to occur in conjunction with a medical procedure utilizing surgical instrument 10. It should be noted that surgical spike 28, in the preferred embodiment as depicted in FIG. 5, is envisioned to be what is commonly known in medical surgery as a Kirschner wire or "K" wire, although other comparable and/or equivalent means are capable of utilization.

As illustrated in FIG. 5, and in keeping with the invention, cylindrical opening 27 of fastening pin 22 has passed therethrough surgical spike 2 such that surgical instrument 10 is anchored in mechanical alignment in conjunction with the bone in question for purposes of achieving the acute angle osteotomy cut.

After so positioning surgical instrument 10 in relationship to surgical spike 28, screw member 26 is rotated so as to allow for the proper angular positioning of indicator arm !7 in relationship to angle member 12 as evidenced by the markings appearing on calibration arm 11. It should further be noted that nothing herein contained should restrict the invention to calibrating same prior to the passing of surgical spike 28 through cylindrical opening 27 of surgical instrument 10, but rather, it is within the scope of the invention to adjust and otherwise set the desired acute angle between guiding edge 16 and guiding edge 21 after surgical spike 28 has been inserted through cylindrical opening 27.

It should further be noted that inherent in the design of this invention is the fact that a smaller incision is required at the point of said surgical procedure as compared with prior medical practices and devices related to same since inherent in the design of surgical instrument 10 is the fact that guiding edge 16 and guiding edge 21 are alignable with respect to each other by the interrelationship between the remaining components of the device which are removed from the point of the surgical procedure.

As further referenced in FIG. 5, upon positioning indicator arm 17 at its appropriate and selected location as related to calibration arm 11, screw member 26 is rotated so as to tighten upon arm member 25 so as to rigidly position indicator arm 17 in relationship to calibration arm 11. In so doing, there is in effect, the selected positioning of guiding edge 16 of aligning member 15 with guiding edge 21 of aligning member 20 so as to define the pre-determined acute angle desired with regard to achieving the acute angle osteotomy cut in the bone in question.

In further keeping with the invention and as illustrated in FIG. 5, surgical instrument 10 is compressed against the bone in question such that spike member 24 is compressed against the surface of said bone thereby providing a second point of anchoring surgical instrument 10 in relationship to the bone in question separate and apart from the mechanical anchoring achieved by the interrelationship between cylindrical spike 28 and fastening pin 22. As a result thereof, there is achieved a mechanical alignment of surgical instrument 10 with regard to the bone in question which is not subject to accidental dislodging or movement so as to cause errors associated with the cutting of the bone in question.

Once surgical instrument 10 is so positioned and anchored in place as discussed above, the acute angle osteotomy cut can now be accomplished in accordance with the invention by causing the cutting implement, be it a saw, or otherwise, to be guided along guiding edge 16 and guiding edge 21.

It should further be noted that the positioning of surgical spike 28 in accordance with the invention, additionally assists the surgeon in utilizing surgical instrument 10 in making said acute angle osteotomy cut in that the vertical extension of surgical spike 28 as illustrated in FIG. 5 defines a vertical plane between itself and guiding edge 16 as well as defining a second vertical plane between itself and guiding edge 21. The relevance of the above is that upon a surgeon seeking to make the cuts along guiding edge 16 and guiding edge 21, said surgeon is presented with the concerns that the cut should be perpendicular to the bone in question and not canted off center. By aligning the plane of the saw blade utilized to accomplish said bone cut with surgical spike 28 as said cut is made, there is achieved means to avoid the tilting and/or canting of said saw blade as the cut is made so as to achieve, in effect, an appropriate vertical cut into said bone. In this fashion, a greater degree of surgical precision is achievable with regard to said cuts as referred to above that was not available with regard to prior art devices and/or procedures.

In keeping with the invention, and as should be obvious from the above, the incision in question is minimal in utilization of surgical instrument 10 since that portion of surgical instrument 10 that is in conjunction with the surgical opening only encompasses the area of surgical instrument 10 defined by pedestal member 14, aligning member 15, pedestal member 19, aligning member 20 and fastening pin 22. Additionally, and as a further feature of the invention in question, surgical instrument 10 allows for the setting of the angle of cut defined between guiding edge 16 and guiding edge 21 by manipulating an indicator arm 17 in relationship to calibration arm 11 as discussed above, same occurring outside of the incision area thus allowing for minimal trauma to the area undergoing said medical procedure.

Additionally, it should further be noted that in conjunction with the operative procedure depicted in FIG. 5 and the utilization of surgical instrument 10 associated therewith, surgical instrument 10 further provides the additional advantage due to its construction in that calibration arm 11 provides, in effect, a handle which can be grasped by the surgeon performing the bone cut which, due to the inherent features of surgical instrument 10 provides a means to steady and otherwise manipulate the positioning of the bone in question as said surgeon utilizes the cutting implement in question be it an electrical rotational saw blade, or otherwise, in his other hand such that upon coordinating both the bone position and the placement of the cutting blade, there is achieved an accurate cut of bone not available by utilizing prior art devices.

In conjunction with the above, it should further be noted that it is also within the scope of the invention, that the utilization of surgical instrument 10 should not only be applicable to providing guidance in the cutting of bone associated with a toe as illustrated in FIG. 5, but rather, is applicable to such cutting as related to any skeletal elements of the body where such incisions are part of a medical procedure.

Additionally, and in further keeping with the invention, it is also within the scope of the invention, although not illustrated in the drawings, to have aligning member 15 and aligning member 20 of surgical instrument 10 define an arched surface as opposed to a flat planar surface as depicted in FIG. 5, said arched planar surface being characteristic of the utilization of surgical instrument 10 in conjunction with application to other bone cutting procedures wherein it is desirous to have said arched surface, in effect, curl around or otherwise conform with the curvature of the bone area undergoing said cutting procedure.

It will be understood that the foregoing general description and the following detailed description as well are exemplary and explanatory of the invention, but are not restrictive thereof.

The accompanying drawings referred to herein and constituting a part hereof, are illustrative of the invention but not restrictive thereof, and, together with the description, serve to explain the principles of the invention.

I claim:

1. A surgical instrument for use in achieving acute angle osteotomy cuts in bone comprising:
    (a) a calibration arm;
    (b) an angle member structurally affixed to said calibration arm and lying within the same plane of said calibration arm;
    (c) a first elevational member, structurally affixed to said angle member and perpendicular to the plane defined by said calibration arm and said angle member;
    (d) a first pedestal member structurally affixed to said first elevational member and perpendicular to said first elevational member;
    (e) a first aligning member structurally affixed to said first pedestal member which further defines a first guiding edge;
    (f) and indicator arm;
    (g) a second elevational member structurally affixed to said indicator arm and perpendicular to said indicator arm;
    (h) a second pedestal member structurally affixed to said second elevational member and perpendicular to said second elevational member;
    (i) a second aligning member structurally affixed to said second pedestal member which further defines a second guiding edge;
    (j) coupling means capable of structurally coupling said first pedestal member to said second pedestal member so as to allow for the pivoting about said coupling means of said first pedestal member with said second pedestal member thereby selectively defining an acute angle capable of guiding, during a surgical procedure, a cutting instrument capable of causing the cutting of a bone; and
    (k) a spike member structurally affixed to said first aligning member.

2. A surgical instrument for use in achieving acute angle osteotomy cuts in bone as set forth in claim 1 wherein said coupling means defines an opening through its center capable of having passed therethrough a surgical wire.

3. A surgical instrument for use in achieving acute angle osteotomy cuts in bone as set forth in claim 2 comprising a fastening means capable of selectively positioning in a predetermined aligned location said indicator arm as related to said calibration arm.

4. A surgical instrument for use in achieving acute angle osteotomy cuts in bone as set forth in claim 2 wherein said calibration arm defines a portion of an arch.

5. A surgical instrument for use in achieving acute angle osteotomy cuts in bone as set forth in claim 2 wherein said first and second aligning members each define a flat surface which is parallel to the plane defined by said calibration arm.

6. A surgical instrument for use in achieving acute angle osteotomy cuts in bone as set forth in claim 2 wherein said first and second aligning members define an arched surface capable of conforming to the curvature of a bone that is undergoing an acute angle osteotomy cut.

7. A surgical instrument for use in achieving acute angle osteotomy cuts in bone as set forth in claim 2 additionally comprising a surgical spike capable of structurally being driven into the bone undergoing an acute angle osteotomy cut and wherein said surgical spike has a cross-sectional dimension capable of passing through the opening formed through said coupling means.

* * * * *